United States Patent [19]

Christian

[11] Patent Number: 4,784,656

[45] Date of Patent: Nov. 15, 1988

[54] FECAL INCONTINENCE RECEPTACLE AND METHODS OF USE

[76] Inventor: Delores J. Christian, 3878 Riveria Dr., San Diego, Calif. 92109

[21] Appl. No.: 45,172

[22] Filed: Apr. 23, 1987

Related U.S. Application Data

[63] Continuation of Ser. No. 729,639, May 2, 1985, abandoned.

[51] Int. Cl.$^4$ .............................................. A61F 5/44
[52] U.S. Cl. ................................... 604/355; 604/332; 604/333; 604/334; 604/342
[58] Field of Search ................................ 604/327–345, 604/355; 4/144.1–144.4, 479, 480, 482, 484

[56] References Cited

U.S. PATENT DOCUMENTS

| | | |
|---|---|---|
| 1,274,143 | 7/1918 | Cook . |
| 2,154,202 | 4/1939 | Gricks .............................. 604/343 |
| 2,519,743 | 8/1950 | Cruise . |
| 2,759,477 | 8/1956 | Mains .............................. 604/343 |
| 3,089,493 | 5/1963 | Galindo . |
| 3,432,865 | 3/1969 | Schwartz . |
| 3,522,807 | 8/1970 | Millenbach . |
| 3,690,320 | 9/1972 | Riely ................................ 604/333 |
| 3,734,096 | 5/1973 | Millenbach . |
| 3,780,739 | 12/1973 | Frank . |
| 3,804,093 | 4/1974 | Fell . |
| 3,825,005 | 7/1974 | Fenton . |
| 3,865,109 | 2/1975 | Elmore et al. . |
| 4,030,500 | 6/1977 | Ronnquist ......................... 604/328 |
| 4,253,460 | 3/1981 | Chen et al. . |
| 4,296,749 | 10/1981 | Pontifex . |
| 4,368,733 | 1/1983 | Sanidas .............................. 604/327 |
| 4,387,713 | 6/1983 | Calanni . |
| 4,411,659 | 10/1983 | Jensen et al. . |
| 4,439,191 | 3/1984 | Hogan .............................. 604/332 |
| 4,445,898 | 5/1984 | Jensen .............................. 604/332 |
| 4,460,363 | 7/1984 | Steer et al. . |
| 4,664,661 | 5/1987 | Ferguson ........................... 604/344 |

FOREIGN PATENT DOCUMENTS 7703562 10/1978 Netherlands ...................... 604/355

Primary Examiner—C. Fred Rosenbaum
Assistant Examiner—Mario Costantino
Attorney, Agent, or Firm—Wood, Herron & Evans

[57] ABSTRACT

A new and improved receptacle for collecting fecal matter from incontinent patients and in particular bedridden incontinent patients is disclosed. The fecal incontinence receptacle comprises generally a gasket for sealingly engaging an area substantially adjacent to a stoma or anus of a wearer to form a liquid-tight seal therebetween, a conduit joined to the gasket for providing a passageway for discharge received from the stoma or anus of the wearer to pass therethrough, and a disposable receptacle detachably connected to the conduit for collecting and disposing of fecal matter received from the conduit. The gasket comprises generally a flexible plastic material having an adhesive coating on one surface with a removeable protective sheet covering the adhesive coating. The receptacle comprises generally an opening at one end for detachably connecting the receptacle to the bottom opening of the conduit. The contents collected in the receptacle may then be disposed of by disconnecting the receptacle from the conduit for disposing of the contents collected therein without disconnecting the gasket from the wearer. A new or previously cleaned receptacle may be connected to the conduit. In addition, preferably the conduit of the fecal collecting receptacle is provided with venting capability for permitting gases accumulated therein to escape therefrom, passage capability for permitting an instrument, such as a thermometer, to be inserted into the receptacle for contact with the wearer and deodorizing capability for deodorizing undesirable odors emanating from the fecal matter collected in the receptacle.

29 Claims, 1 Drawing Sheet

FECAL INCONTINENCE RECEPTACLE AND METHODS OF USE

This application is a continuation of application Ser. No. 729,639, filed May 2, 1985, now abandoned.

FIELD OF THE INVENTION

The present invention relates generally to a fecal incontinence collecting device and more particularly to an incontinence device for collecting fecal matter from the anus of a person.

BACKGROUND OF THE DISCLOSURE

A number of fecal collection bags for incontinent patients have heretofore been provided in attempts to eliminate the mundane evils and inefficiencies associated with the care for incontinent patients and in particular bedridden incontinent patients. Even though such devices have been welcomed by the medical profession with optimism and enthusiasm, the fecal collection bags provided hitherto have not been without their disappointments or drawbacks.

One major problem with such devices concerns the formation of an ineffective seal about the stoma or anus. Such a disadvantage is generally manifested by leakage, unintentional detachment and discomfort to the patient during use. A second major problem concerns the limited capacity generally associated with such fecal collection bags. In particular, the fecal bags provided hitherto are changed with regularity out of necessity to avoid the dreaded consequences that occur from trying to remove overly filled bags. A third major problem concerns the formation and accumulation of gas within such fecal collection bags and the undesirable inflation, discomfort and odors associated therewith. Provisions therefore have been made to permit the gas which has accumulated within the device to escape therefrom. Presently, the practices for releasing accumulated gas from such devices include either providing the device with a form of venting or requiring the nurse or wearer to unstick the ring from the skin around the stoma or anus. Unfortunately, because of the necessity for continuously unsticking the ring from the skin of a wearer, this can lead to excess irritation, or if venting is provided with each disposable bag, this can be quite expensive. A fourth major problem encountered by a wearer of such bags is the undesirable odors emanating from the fecal material collected in the bags. At the present time, the most common remedy to combat such odors is to either replace the device, remove it and empty its contents, or provide deodorizing capability with each disposable bag. Obviously, this problem and these solutions can greatly inconvenience, embarrass and increase the cost to the wearer.

While numerous attempts in the past have been made to correct the shortcomings discussed above, the disadvantages stated are still encountered with the fecal incontinence bags available today. Consequently, there exist definite needs for an economical fecal incontinence receptacle that can effectively and conveniently eliminate the above mentioned problems.

SUMMARY OF THE INVENTION

In brief, the present invention seeks to alleviate the above indicated problems and shortcomings of the present state of the art and is directed to a new and improved incontinence receptacle for collecting fecal matter from incontinent patients and in particular bedridden incontinent patients. In a preferred form, the fecal collecting receptacle comprises a gasket designed to sealingly engage an area contiguous or substantially contiguous to a stoma or anus of a person to form a liquid tight seal therebetween, a conduit joined to the gasket designed to provide a passageway for discharge received from a stoma or anus of a person to pass therethrough, and a disposal receptacle detachably connected to a conduit for collecting and disposing of discharge received from the conduit. More particularly, the gasket generally comprises a soft, pliable, stretchable and contractable plastic material having first and second opposite side surfaces and having outer and inner marginal edges. The inner edge of the gasket defines an aperture for communicating with the stoma or anus of a person to permit discharge from the stoma or anus to pass therethrough and into the conduit. The first surface of the gasket is coated preferably with an adhesive and has a removeable protective sheet covering the adhesive during nonuse. The conduit generally comprises top and bottom ends having an opening at each end thereof to define the passageway. The second surface of the gasket is generally secured in a liquid-tight fashion to the conduit about the top opening of the conduit. As to the receptacle, it is preferably disposable having an opening at one end for sealingly and removeably connecting to the conduit about the bottom opening.

Thusly, the present invention contemplates a novel system employing a conduit connected in a liquid-tight fashion to a gasket for providing a passageway for fecal matter discharged from the stoma or anus of a person. In addition, a reusable or disposable receptacle is connected in a liquid-tight manner to the conduit for receiving the discharge being passed through the conduit. Such a novel receptacle enables the wearer or attendant, such as a nurse, to advantageously disconnect the receptacle from the conduit for disposal of the contents collected therein without first having to disconnect the gasket from the skin of the wearer. Therefore, the present invention enables the wearer or attendant to either replace the receptacle or to remove it and empty its contents with minimal irritation, inconvenience and at a reduced cost.

In a further feature of the present invention, the fecal incontinence receptacle provides a bag which automatically releases gas discharged from the stoma or anus to the environment thereby eliminating undesirable inflation of the bag.

In another feature of this invention resides in providing a bag which is furnished with deodorizing capability for deodorizing the fecal matter collected in the receptacle.

In still another feature, the present invention provides a passage for the insertion of an instrument, such as a thermometer, into the receptacle for contact with the wearer without first having to unstick the gasket from the wearer. The venting, passage and deodorizing means preferably are located on or in the conduit. By locating the venting, deodorizing and passage means on or in the conduit, this invention provides for an economical system which reduces the number of such means required for use with each disposable receptacle. Thus, the advantages of such means can still be enjoyed by the wearer and attendant without the prohibitive costs associated with such means.

In yet another feature of the present invention, the fecal incontinence receptacle is designed to accumulate and hygienically store all consistencies excreted by an incontinent person until such time when it is convenient to dispose of such matter. Thus, the present invention virtually eliminates the problem of soiled beds due to insufficient means of containing fecal matter defecated by incontinent persons, skin excoriation caused by continued contact with fecal matter, and complications, inconveniences and embarrassment arising from inadequate means of containment of fecal material.

In still a further feature of the present invention, the shape, size and construction of the device are uniquely advantageous, since these features keep the conduit, which is immediately adjacent to the wearer, empty so that the wearer can turn and move freely without the fear of rolling directly onto a receptacle full of feces as is currently experienced with the fecal collecting devices provided heretofore.

In a further feature of the present invention is to provide a fecal incontinence receptacle which is simple and inexpensive to construct and maintain and wherein the above-mentioned modifications can be accomplished.

Thus, it can be appreciated that the special features and advantages of this fecal incontinence receptacle makes it a unique device for collecting and disposing of fecal matter in the most convenient, economical and pleasant manner.

The above and other features and advantages of the invention, including various novel details of construction and combination of parts, will be now particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings which are shown illustrative embodiments of the invention from which the novel features and advantages will be apparent.

DETAILED DESCRIPTION

Figure 1:
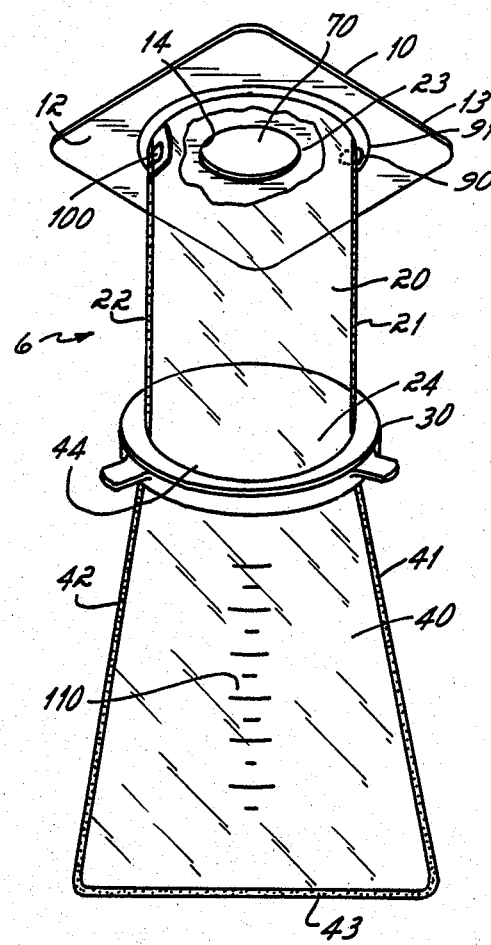
FIG. 1 is a perspective view of one form of a fecal incontinence receptacle which is illustrative of an embodiment of the invention, various background lines which would normally be seen through the receptacle have not been shown for clarity.

By way of illustrating and providing a better appreciation of the present invention, the following detailed description is given concerning the fecal incontinence receptacle of the invention and methods of use thereof.

Referring now to the drawings, the numeral 6 generally designates a fecal collector and more particularly an anal fecal collector comprising attaching means or a gasket 10, conduit means or a cylinder 20, coupling means 30 and a receptacle 40. In a preferred embodiment depicted, the receptacle 40 and cylinder 20 are each formed essentially from, for instance, two sheets of odor-barrier thermoplastic film heat-sealed together along their side edges 41 and 42 or 21 and 22, respectively. In addition, the distal end 43 of the receptacle 40 is heat-sealed together to form the receptacle 40 having an opening 44.

It is also contemplated by this invention that receptacle 40 and cylinder 20 may be made of any suitable fluid impervious, odor-barrier film or plastic. For example, flexible walls of the receptacle and cylinder may be continuous and formed of a polyolefin film laminated with an appropriate gas-barrier film. A particularly suitable commercial material comprises low-density polyethylene coextruded with a coextensive layer or core of polyvinylchloride; but, of course, any of a wide variety of other suitable materials may be employed. It should also be appreciated that cylinder 20 and receptacle 40 may be formed by any process and of any shape so long as the process for forming and the shape of the cylinder 20 and receptacle 40 are not inconsistent with the teachings of this invention.

The attaching means or gasket 10 is formed preferably of soft, flexible, stretchable closed-cell thermoplastic foam having normal planar opposite sides 11 and 12, and preferably having generally a circular or rectangular outer marginal edge 13 and a circular inner marginal edge 14, as depicted in FIG. 1. A closed-cell foam of polyethylene having a thickness within the general range of about 2 to about 10 millimeters, and preferably about 3 millimeters is particularly effective. However, any other thermoplastic foam material, such as polyurethane, or any other suitable plastic sheet material having the described properties of such foam, i.e., softness, pliability, stretchability and contractability, may be used.

Figure 5:
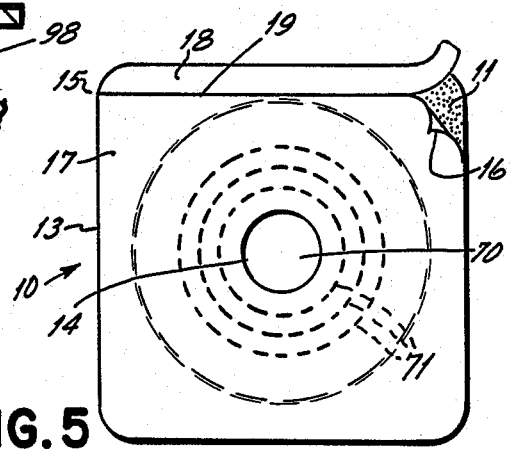
FIG. 5 is a top plan view of a gasket for attaching a fecal incontinence receptacle to a patient which is illustrative of an embodiment of the invention.

The surface of side 11 of gasket 10 is preferably coated with a layer of any pressure-sensitive and water-resistant medically approved adhesive. The tacky adhesive coating is in turn covered by a protective removeable release sheet 15. The protective covering 15 may be made of, for instance, paper having one side 16 suitably coated with a release layer to permit the protective release sheet 15 to be peeled away from the adhesive coating on the surface of side 11 of gasket 10 to expose the adhesive coating. For example, a polyethylene coating on the paper, to which a silicone coating is applied, is effective, but it should be recognized that other coating materials, such as waxes and the like may be used. As illustrated in FIG. 5, the protective removeable release sheet 15 has an overall shape and size conforming with the surface of side 11 of gasket 10. In a preferred embodiment depicted in FIG. 5, the protective removeable release sheet 15 comprises major and minor sections 17 and 18, respectively, divided by a tear or separation line 19 to permit the protective removeable release sheet 15 to be easily removed from the adhesive coating on the surface of side 11 of gasket 10.

With respect to the inner marginal edge 14 as depicted in FIG. 1, it defines a generally circular aperture 70 that is substantially the same size and shape designed to generally surround a stoma or anal opening of a person. Aperture 70 is preferably directly aligned with opening 23 at the top end of cylinder 20 for passing discharge from the stoma or anus into cylinder 20. Cylinder 20 and gasket 10 may be permanently secured together along the inner marginal edge 14 on side 12 of gasket 10 in any suitable manner. Preferably, however, the top end opening 23 of cylinder 20 is secured along a narrow zone adjacent to the inner marginal edge 14 and spaced substantial from the outer marginal edge 13 on side 12 of gasket 10 as illustrated in FIG. 1. When both the cylinder 20 and gasket 10 are formed of thermoplastic material, the two may be heat-sealed together. Regardless of how cylinder 20 and gasket 10 are joined together, a liquid-tight seal should be formed therebetween.

In a further feature of the present invention, aperture 70, if necessary, may be enlarged to accommodate patients with larger stomas or anal openings. To enlarge aperture 70, the procedure simply involves cutting gasket 10 and protective release sheet 15 along any one guideline 71 provided on the protective release sheet with, for instance, a pair of surgical shears prior to the removal of the protective release sheet 15 from gasket 10. Of course, those readily versed in the art will appreciate that a sufficient space, preferably equal to the space utilized by guidelines 71, between the inner marginal edge 14 and the zone of attachment of cylinder 20 should be left available to permit gasket 10 and protective release sheet 15 to be freely cut for enlarging aperture 70 without cutting into cylinder 20 during the enlargement procedure. It should be further understood, however, that even though specific reference is made herein to stomas or anal openings, the fecal incontinence receptacle of the present invention is also suitable for use, if appropriate, with any opening, surgically created or otherwise, where there is a need to collect matter discharged therefrom. In other words, stoma is used in a broad sense herein to include all such openings.

Figure 2:
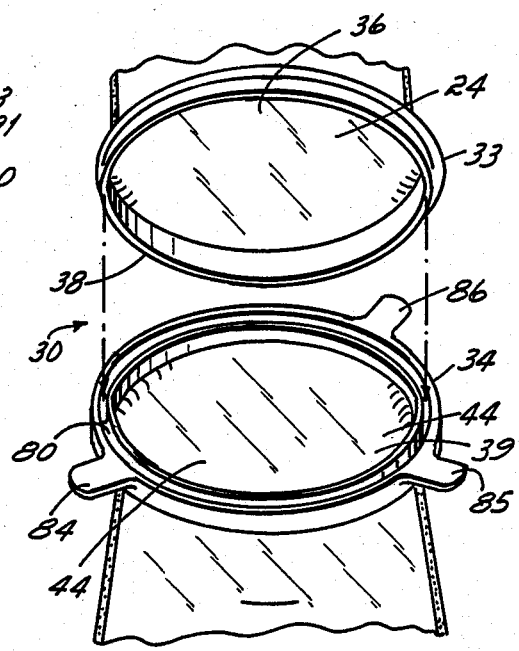
FIG. 2 is a disassembled perspective view of one form of a removeable connector which is illustrative of an embodiment of the invention.
Figure 3:
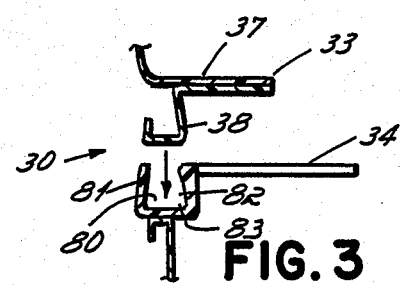
FIG. 3 is a cross sectional exploded view of the removeable connector of FIG. 2 which is illustrative of an embodiment of the invention.

Turning now to a discussion of the coupling means, it is generally depicted by numeral 30 in FIGS. 1–3 and comprises first and second coupling members 33 and 34, respectively. The first coupling member 33 is preferably circular, is secured, for instance, by heat-sealing the coupling member 33 about the bottom opening 24 of cylinder 20 to form a liquid-tight seal therebetween, has a central aperture 36, has an outwardly-extending flange 37, and has a downwardly-extending interlocking annular rib 38. The annular rib 38 preferably is integrally molded with flange 37, is hook-shaped and is turned inwardly towards cylinder 20.

The second coupling member 34 is also illustrated in FIGS. 1–3 and is secured by heat-sealing it about the opening 44 of receptacle 40 to form a liquid-tight seal therebetween. The second coupling member 34, like the first coupling member 33, is preferably circular, defines aperture 39 for permitting the discharge to pass from cylinder 20 into receptacle 40 and has an annular channel 80.

As shown in detail FIG. 3, the second coupling member is of channel-shape 80 having tapered inner and outer walls 81 and 82, respectively, terminating at base 83. The inner and outer walls 81 and 82 together with base 83 define the restricted annular channel 80 corresponding to the annular hook-shaped rib 38. In use, the annular hook-shaped rib 38 of the first coupling member 33 is firmly depressed or snapped into the corresponding annular channel 39 of the second coupling member 34 to connect together in a liquid-tight fashion the first and second coupling members. Three ears 84, 85 and 86 as depicted in FIGS. 1 and 2 are secured to or molded integrally with the outer tapered wall 82 of the annular channel 80. Each of the three ears 84, 85 and 86 may serve to be gripped and pulled by the wearer when it is desirable to separate receptacle 40 from cylinder 20, for instance, without first having to unstick gasket 10 of cylinder 20 from the patient. The ears 84, 85 and 86 may also assist in the attachment of receptacle 40 to cylinder 20. For convenience of the wearer, the ears 84, 85 and 86 may be located at any position around the axis of the second coupling member 34. Preferably, each coupling member is formed from a resilient, plastic material. However, any suitable material made be employed.

Figure 4:
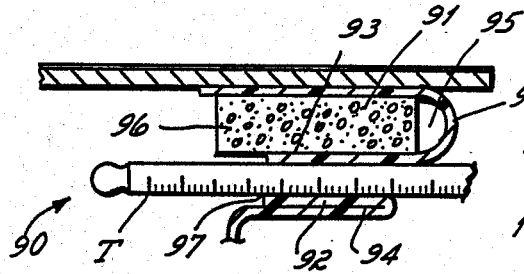
FIG. 4 is a cross sectional exploded view of a thermometer insertion port which is illustrative of an embodiment of the invention, the thermometer being inserted therethrough.

In still another feature of the present invention, as illustrated in FIGS. 1 and 4, the cylinder 20 is further provided with passage means, venting means and deodorizing means referred to generally as numerals 90, 91 and 100, respectively. More specifically as shown in FIG. 4, the sheets at edge 22 of cylinder 20 are contoured to define a depending tab or flap 92 and 93. Prior to heat-sealing of the panels, flaps 92 and 93 are folded upwardly and inwardly to define pockets 94 and 95, respectively. A foam pad 96 is inserted into one or both of the pockets 95 and, during a final heat-sealing operation, the sheets and flaps are heat-sealed together to define a normally closed passage 97 between opposed flaps 92 and 93 of the respective sheets. Venting means 91, in the form of one or more pinholes 98, are formed in the wall of pocket 95 that retains the resilient foam pad 96. The pad performs the functions of restraining the outflow and solids through venting 98 without at the same time preventing the escape of gases, and of exerting a gentle force against flap 93 to maintain passage 97 in closed condition when not in use (not shown). To the extent that the excretory contents of the bag may enter and expand pockets 94 and 95, the walls of passage 97 tend to be sealed even more tightly in use. Because of this construction, in cases where access to the rectal area becomes necessary for purposes of inserting a thermometer T or other medical instrument, such a procedure may be carried out without having to first detach cylinder 20 or receptacle 40 from the patient simply by inserting the instrument through passage 97 as depicted in FIG. 4 and into contact with the patient. For a more detailed discussion of such passage and venting means, they are more fully described in U.S. Pat. No. 4,445,898, and the entire contents and teachings including the attaching ring of U.S. Pat. No. 4,445,898 is incorporated herein by reference.

In general, any of a number of suitable deodorizing means referred to generally as numeral 100 in FIG. 1 may be utilized. A preferred deodorizing means, however, comprises a disinfecting packet containing a deodorizing composition positioned within the interior of cylinder 20. Such a disinfecting packet is described in complete detail in U.S. Pat. No. 3,690,320, and said U.S. patent is incorporated in its entirety herein by reference. With respect to the types of disinfectant compositions that can be packaged within the disinfecting packet, any number of suitable deodorizing compositions may be used. For example, various solids or pelletized compositions, liquid compositions, and gels can be employed. Numerous such compositions have been heretofore described. A preferred deodorizing formulation comprises the various air-treating gels described in detail in U.S. Pat. No. 2,691,615, and this U.S. patent likewise is incorporated in its entirety herein by reference.

It should be understood to those skilled in the art that even though the above passage, venting and deodorizing means have been described, any suitable passage, venting and deodorizing means may be employed so long as they are not inconsistent with the teachings of this invention. It will also be appreciated that although the passage, venting and deodorizing means may be located in any suitable position, it is especially preferable to locate the passage, venting and deodorizing means on or in cylinder 20. Such a strategic location not only is practical from a use standpoint but extremely economical as well. By locating such means on or in the cylinder 20, the useable life of passage, venting and deodorizing means may be prolonged since only receptacle 40 will be disconnected and discarded. The cylinder 20 housing the passage, venting and deodorizing means will remain secured to the patient for continuous use. This advantage obviously provides a reduction in the number of passage, venting and deodorizing means required and therefore improves the economy of the present invention.

The cylinder 20 and receptacle 40 are preferably about 10 inches and 8 inches in length, respectively, however, the cylinder and receptacle may be of any suitable length or combination of lengths. Further, the receptacle preferably has the capacity for collecting preferably about 1,000 millimeters of discharge to minimize the frequency in which the receptacle needs to be changed. It should be appreciated, however, that the size and capacity of the receptacle should not be too large, or the cylinder excessively long, since the volume collected therein may become excessively heavy leading to possible accidental detachment of the gasket from the wearer. As a further convenience, the receptacle may be volumetrically calibrated by markings 110 to assist in the determination of the volume of discharge passed by the patient, as depicted in FIG. 1.

The operation of the fecal incontinence receptacle of the present invention is simple. When the device is utilized to collect discharge from a stoma or anus of a wearer, any hair present in the area should first be carefully clipped and trimmed as close to the skin as possible, and the skin adjacent to the stoma or anus should be washed with, for instance, a skin cleanser or mild soap and rinsed thoroughly to remove any residue remaining on the skin. The entire area should be thoroughly dried before attaching the fecal collector. Once the area has been dried, the wearer's stoma or anus is sized so that aperture 70 can be prepared to conform thereto. After sizing and preparing aperture 70, the protective removeable release sheet 15 is removed from gasket 10 via bending gasket 10 along the tear or separation line 19 to permit the major and minor sections 17 and 18 of protective release sheet 15 to be peeled away from the gasket 10. After the removal of the protective release sheet 15, the application of gasket 10 to, for instance, the wearer's buttocks is evident, i.e., gasket 20 is inserted between the buttocks and flexibly conforms to the curvature with aperture 70 encompassing the anus and being marginally contiguous or substantially contiguous therearound. The remainder or adhesive portion of the gasket adheres to the wearer's buttocks to further insure retention of the device and to form a liquid-tight seal therebetween. The gasket 10 and cylinder 20 may be mounted on the wearer with or without receptacle 40 being connected to cylinder 20.

During use, the wearer passes discharge through aperture 70 of gasket 10 and into cylinder 20. The cylinder 20 acts as a passageway for the discharge to travel which eventually is collected in receptacle 40. As indicated above, a thermometer or other instrument may be inserted into the cylinder through passage means 90 for contact with the wearer, gas may escape from the device through the venting means 91 without having to unstick the gasket, and the unpleasant odor emanating from the fecal matter collected in the receptacle may be deodorized via the deodorizing means 100 provided within the conduit.

After use, it is not necessary to unstick the gasket from the patient to discard the fecal matter collected in receptacle 40. It is only necessary to remove receptacle 40 from cylinder 20 and discard either the receptacle and the contents contained therein, or empty the receptacle for cleaning. A new or previously used but clean receptacle 40 may be reconnected to the already mounted cylinder 20 without having to first unstick the gasket from the wearer. The present device therefore provides the added advantage of reducing the number of times the gasket needs to be stuck and unstuck to and from the wearer decreasing the irritation on human skin presently experienced with fecal devices provided heretofore. Further, the present invention provides additional economy since by locating the venting, passage and deodorizing means in or on the conduit, it reduces the number of such means required with the devices currently available.

The present invention may be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

What is claimed is:

1. A portable fecal incontinence receptacle for collecting discharge for an anus of a bed-ridden or ambulatory person comprising a gasket for sealingly engaging an area substantially adjacent to an anus of a bedridden or ambulatory person to form a liquid-tight seal therebetween, aid gasket comprising soft, pliable, stretchable and contractable plastic material having first and second opposite side surfaces and having outer inner marginal edge for permitting said gasket to conform to the curvatures between the buttocks when said gasket is inserted therebetween, the inner edge defining an aperture for communicating with an anus of a bedridden or ambulatory person to permit discharge from an anus of a bedridden or ambulatory person to pass therethrough, the first surface being coated with an adhesive and having a removable protective sheet covering the adhesive coating of said gasket, conduit means for permitting discharge received from an anus of a person to pass therethrough, said conduit means having first and second ends and extending on the order of about 10 inches in length between the ends and having openings at each end thereof to define a passageway, the second surface of said gasket being secured to said conduit means about the first opening thereof to form a liquid-tight seal therebetween so as to form a passageway through the aperture formed by the inner edge of said gasket and the first opening of said conduit means, said conduit means being provided with venting means along a portion thereof for permitting a gas released into said portable fecal incontinence receptacle to escape therefrom, and a disposable receptacle comprised of a flexible plastic material for collecting and disposing of on the order of about 1,000 milliliters of discharge received from said conduit means, said disposable receptacle having an opening at one end thereof sealingly and removeably connected along the second opening of said conduit means whereby, upon removal of the protective sheet, said gasket may be sealed to an area about an anus of a bedridden or ambulatory person, and upon passage of discharge from the anus, the discharge may pass through the aperture of said gasket and the passageway of said conduit means into said receptacle for disposal thereof whereby, upon use, said portable fecal incontinence receptacle may be worn by a person while bedridden or ambulatory without substantially obstructing flow of discharge into said disposable receptacle or requiring additional support when said disposable receptacle is in an emptied or filled state.

2. A portable fecal incontinence receptacle of claim 1 wherein said conduit mean is comprised of a flexible plastic material 3. A portable fecal incontinence receptacle of claim 2 wherein the flexible plastic material is a flexible thermoplastic material.

4. A portable fecal incontinence receptacle of claim 2 wherein said conduit means comprises a pair of panels of the flexible plastic material having marginal edges, the panels being joined at their marginal edges to form the passageway.

5. A portable fecal incontinence receptacle of claim 1 wherein the second surface of said gasket is attached to said conduit means about the first opening thereof with a heat seal.

6. A portable fecal incontinence receptacle of claim 1 wherein said conduit means includes passage means for inserting an instrument into said conduit means.

7. A portable fecal incontinence receptacle of claim 1 wherein said conduit means includes deodorizing means for masking any unpleasant odor within said conduit means.

8. A portable fecal incontinence receptacle of claim 1 wherein said disposable receptacle comprises a flexible thermoplastic material.

9. A portable fecal incontinence receptacle of claim 1 further comprising coupling means for removably connecting said receptacle to said conduit means.

10. A portable fecal incontinence receptacle of claim 9 wherein said coupling means comprises a first annular coupling member secured to said receptacle about the opening thereof and having structure to receive a second annular-coupling member secured to said conduit means about the second opening thereof to form a liquid-tight therebetween.

11. A portable fecal incontinence receptacle of claim 10 wherein one of the annular coupling members includes a first annular engaging element and the other coupling member includes a second annular engaging element, the first annular engaging element being dimensioned to sealingly engage the second annular engaging element, the first annular engaging element having at least one pull tab extending outwardly therefrom to enable a person to grasp the pull tab with his fingers for assisting the person in connecting and disconnecting the annular coupling members to and from each other, respectively.

12. A portable fecal incontinence receptacle of claim 11 wherein the first engaging element is a channel and the second engaging element is a projection wherein the channel is dimensioned to sealingly engage the projection to hold the projection securely therein.

13. A portable fecal incontinence receptacle of claim 12 wherein the channel is formed on the first coupling member and the projection is formed on the second coupling member.

14. A portable fecal incontinence receptacle of claim 10 wherein each coupling member is formed of a resilient plastic material.

15. A portable fecal conduit for draining discharge form an anus of a bedridden or ambulatory person into a disposable receptacle comprising a gasket for sealingly engaging an area substantially adjacent to the anus of a person to form a liquid-tight seal therebetween, said gasket comprising soft, pliable, stretchable and contractable plastic material having first and second opposite side surfaces and having outer and inner marginal edges for permitting said gasket to conform to the curvatures between the buttocks when said gasket is inserted therebetween the inner edges defining an aperture for communicating with an anus of a bedridden or ambulatory person to permit discharge from an anus of a bedridden or ambulatory person to pass therethrough, the first surface being coated with an adhesive and having a removable protective sheet covering the adhesive coating of said gasket, and conduit means formed of a flexible plastic material having first and second ends and extending on the order of about 10 inches in length between the ends and having openings at each end thereof to form a passageway for permitting discharge from the anus of a bedridden or ambulatory person to pass therethrough the second surface of said gasket being secured to said conduit means about the first opening thereof to form a liquid-tight seal therebetween so as to form a passageway through the aperture formed by the inner edge of said gasket and the first opening of said conduit means, the first opening of said conduit means being in communication with the aperture of said gasket and the second opening of said conduit means including means to be sealingly and removably connected to a disposal receptacle for communicating the anus of a bedridden or ambulatory person with a disposable receptacle, said conduit means being provided with venting means along a portion thereof for permitting a gas released into said conduit when connected to a disposable receptacle to escape therefrom whereby, upon removal of the protective sheet, said gasket may be sealed to an area about the anus of a bedridden or ambulatory person, and upon passage of discharge from anus, the discharge may pass through the apertures of said gasket and the passageway of said conduit means into a disposable receptacle removeably and sealingly connected to said conduit means for disposal of the discharge collected in the receptacle and, when connected to the disposable receptacle, said portable fecal conduit may be worn by a person while bedridden or ambulatory without substantially obstructing flow of discharge into the disposable receptacle or requiring additional support when said conduit is connected or disconnected to a disposable receptacle.

16. A portable fecal conduit of claim 15 wherein the conduit means comprises a flexible thermoplastic material.

17. A portable fecal conduit of claim 15 wherein said conduit means comprises a pair of panels of the flexible plastic material having marginal edges, the panels being joined at their marginal edges to form a passageway.

18. A portable fecal conduit of claim 15 wherein said conduit means includes passage means for inserting an instrument into said conduit means.

19. A portable fecal conduit of claim 15 wherein said conduit means includes deodorizing means for masking any unpleasant odor within said conduit means.

20. A portable fecal conduit of claim 15 wherein the second surface of said gasket is attached to said conduit means about the first opening thereof with a heat seal.

21. A fecal conduit of claim 15 wherein said conduit means includes an annular coupling member secured about the second opening thereof and having means to sealingly receive a corresponding annular coupling member secured about an opening of a receptacle to form a liquid-tight closure therebetween.

22. A portable fecal incontinence receptacle for collecting discharge form an anus of a bedridden or ambulatory person providing the sanitary disposal thereof comprising a gasket for sealingly engaging an area substantially adjacent to an anus of a bedridden or ambulatory person to form a liquid-tight seal therebetween, said gasket comprising soft, pliable, stretchable and contractable plastic material having first and second opposite side surfaces and having outer and inner marginal edges for permitting said gasket to conform to the curvatures between the buttocks when said gasket is inserted therebetween, the inner edge defining an aperture for communicating with an anus of a bedridden or ambulatory person to permit discharge from an anus of a bedridden or ambulatory person to pass therethrough, the first surface being coated with an adhesive and having a removable protective sheet covering the adhesive coating of said gasket, conduit means for permitting discharge received from an anus of a bedridden or ambulatory person to pass therethrough, said conduit means comprising a pair of panels of a flexible plastic material having marginal edges, the panels being joined at their marginal edges, said conduit means having first and second ends extending on the order of about 10 inches in length between the ends and having openings at each end there of to define a a passageway, the second surface of said gasket being secured to said conduit means about the first opening thereof to form a liquid-tight seal therebetween so as to form a passageway through the aperture formed by the inner edge of said gasket and the first opening of said conduit means, said conduit means being provided with venting means along a portion thereof for permitting a gas released into said portable fecal incontinence receptacle to escape therefrom, a disposable receptacle for receiving on the order of about 1000 milliliters of discharge from said conduit means and for the sanitary disposal thereof, said receptacle comprising flexible plastic material having an opening at one end thereof, and annular coupling means for removeably connecting said receptacle to said conduit means and providing a liquid-tight closure therebetween, said annular coupling means comprising a first annular coupling member secured to said disposable receptacle about the opening thereof including structure to receive a second annular coupling member secured to said conduit means about the second opening thereof wherein one of the annular coupling members includes a first annular engaging element and the other annular coupling member includes a second annular engaging element, the first annular engaging element being dimensioned to sealingly engage the second annular engaging element, the first annular engaging element further having at least one pull tab extending outwardly therefrom to enable a person to grasp the pull tab with his fingers for assisting the person in connecting or disconnecting the annular coupling members to and from each other, respectively, whereby, upon removable of the protective sheet, the first surface of said gasket may be seated to an area substantially adjacent to an anus of a bedridden or ambulatory person to form a liquid-tight seal therebetween, and upon passage of discharge from the anus, the discharge may sanitarily pass through the aperture of said gasket and the passageway of said conduit means into said disposable receptacle whereby the disposable receptacle may be disconnected from said conduit means and the discharged collected therein may be sanitarily disposed thereof and, upon use, said portable fecal incontinence receptacle may be worn by a person while bedridden or ambulatory without substantially restricting movement of the person or obstructing flow of discharge into said disposable receptacle or requiring additional support when said conduit is connected or disconnected to a disposable receptacle.

23. A portable fecal incontinence receptacle of claim 22 wherein the second surface of said gasket is attached to said conduit means about the first opening thereof with a heat seal.

24. A portable fecal incontinence receptacle of claim 22 wherein the flexible plastic material is a flexible thermoplastic material.

25. A portable fecal incontinence receptacle of claim 22 wherein said conduit means includes passage means for inserting an instrument into said conduit means.

26. A portable fecal incontinence receptacle of claim 22 wherein said conduit means includes deodorizing means for masking any unpleasant odor within said conduit means.

27. A portable fecal incontinence receptacle of claim 22 wherein the first engaging element is a channel and the second engaging element is a projection wherein the channel is dimensioned to sealingly engage the projection to hold the projection securely therein.

28. A portable fecal incontinence receptacle of claim 27 wherein the channel is formed on the first coupling member and the projection is formed on the second coupling member.

29. A portable fecal incontinence receptacle of claim 22 wherein each coupling member is formed of a resilient plastic material.

* * * * *